United States Patent [19]
Ramella

[11] Patent Number: 5,048,514
[45] Date of Patent: Sep. 17, 1991

[54] INHALER FOR MEDICAMENTS CONTAINED IN CAPSULES

[75] Inventor: Luca Ramella, Milan, Italy

[73] Assignee: Somova S.p.A., Milan, Italy

[21] Appl. No.: 547,180

[22] Filed: Jul. 3, 1990

[30] Foreign Application Priority Data

Jul. 7, 1989 [IT] Italy .................. 21132 A/89

[51] Int. Cl.⁵ .............................. A61M 15/00
[52] U.S. Cl. .................. 128/203.21; 128/203.15
[58] Field of Search ............ 128/203.15, 203.21, 128/203.12

[56] References Cited

U.S. PATENT DOCUMENTS

| | | | |
|---|---|---|---|
| 3,848,773 | 11/1974 | Adler et al. | 128/203.21 |
| 3,870,046 | 3/1975 | Elliott | 128/203.15 |
| 3,918,451 | 11/1975 | Steil | 128/203.21 |
| 3,991,761 | 11/1976 | Cocozza | 128/203.21 |
| 4,013,075 | 3/1977 | Cocozza | 128/203.21 |
| 4,116,195 | 9/1978 | James | 128/203.21 |
| 4,627,432 | 12/1986 | Newell et al. | 128/203.21 |
| 4,811,731 | 3/1989 | Newell et al. | 128/203.15 |
| 4,860,740 | 8/1989 | Kirk et al. | 128/203.15 |
| 4,889,114 | 12/1989 | Kladders | 128/203.15 |

Primary Examiner—Aaron J. Lewis
Attorney, Agent, or Firm—Wenderoth, Lind & Ponack

[57] ABSTRACT

A device for the administration of inhalation medicament held in a capsule has a chamber adapted to receive a capsule and provided with an air inlet and an air outlet, capsule piercing elements and a magazine for holding a plurality of capsules. The magazine is rotatably mounted about the air outlet and there is provided a loading mechanism to convey a capsule from the magazine to the chamber.

11 Claims, 5 Drawing Sheets

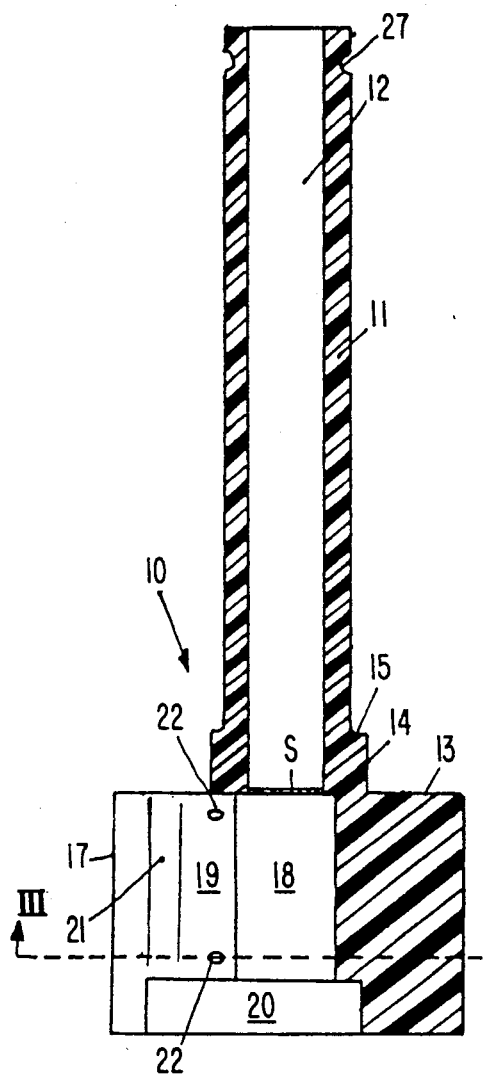
Fig. 1
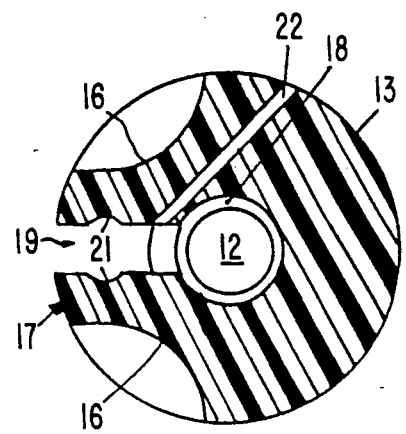
Fig. 3
Fig. 2
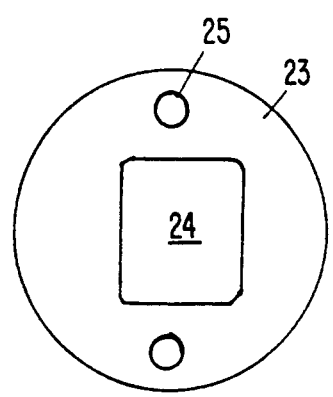
Fig. 5
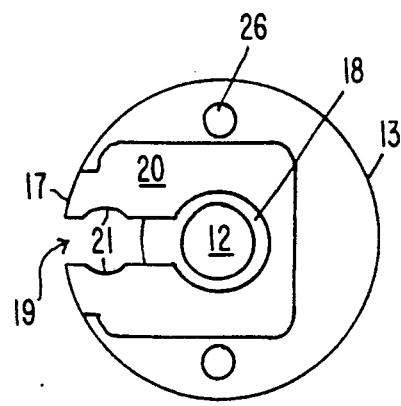
Fig. 4

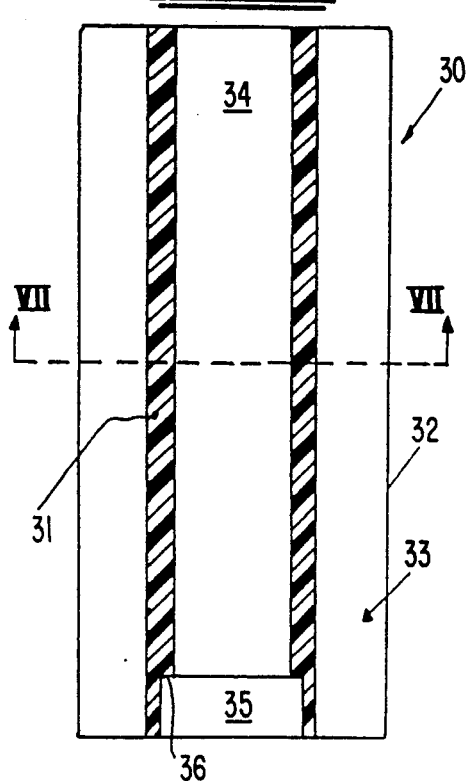
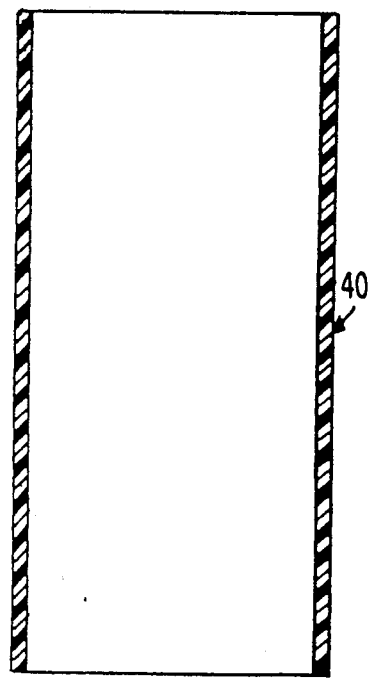
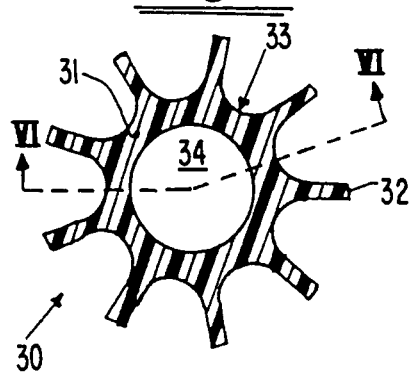
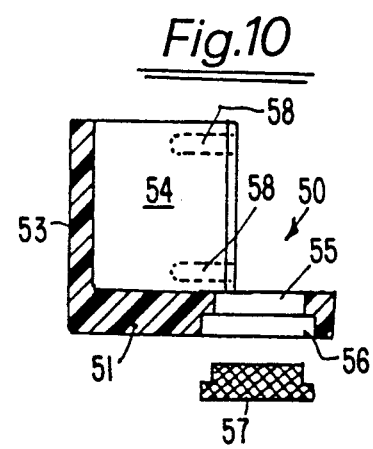
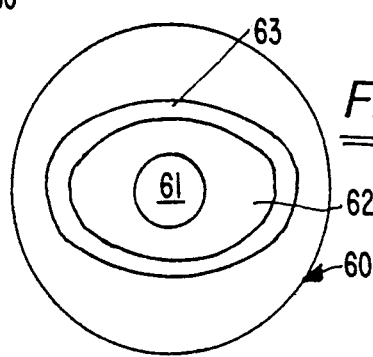
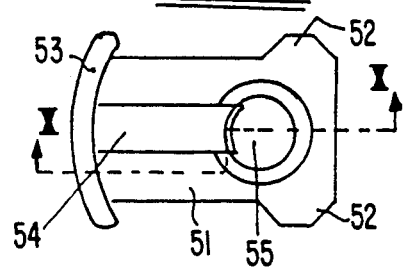

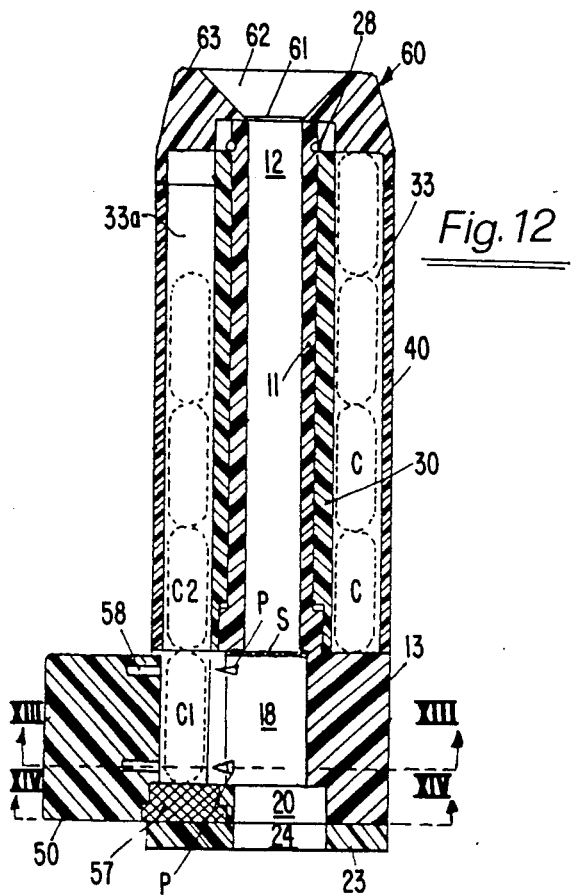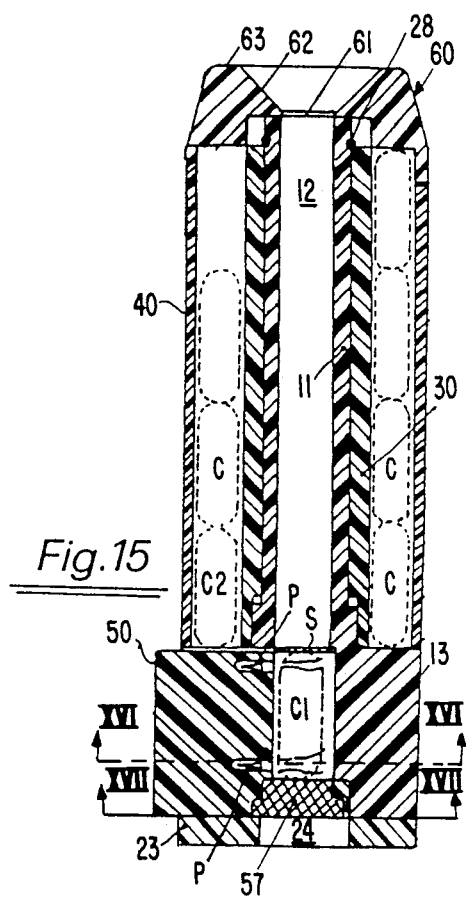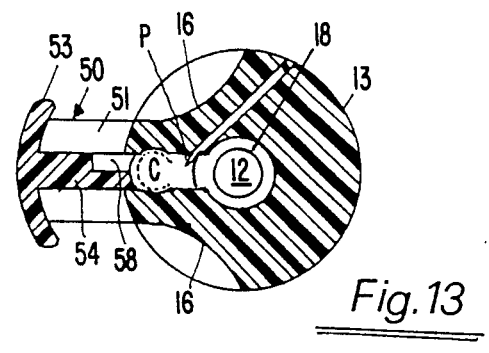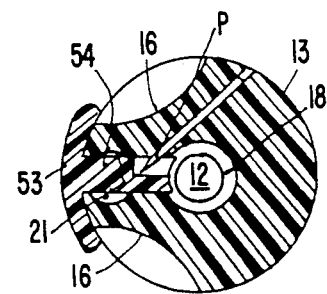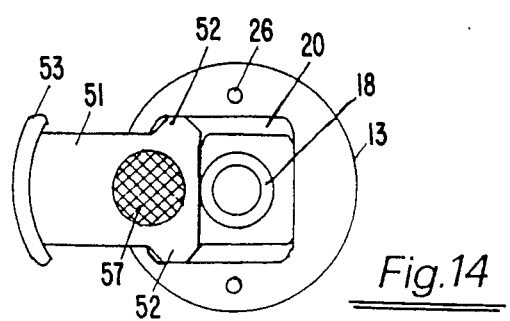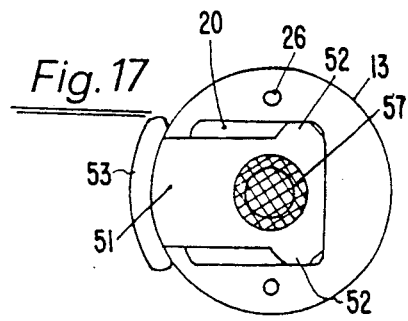

5,048,514

INHALER FOR MEDICAMENTS CONTAINED IN CAPSULES

BACKGROUND OF THE INVENTION

1. Field of the Invention

This invention relates to a medicament inhalation device, more particularly to such a device for the inhalation of medicaments hel in capsules prior to administration.

2. Description of the Related Art

U.S. Pat. No. 3,991,761 discloses a device of this type, which comprises two pivotally connected portions defining a chamber into which a capsule is placed horizontally after which its ends are pierced by two needles. Inhalation through a mouthpiece imparts a spinning motion to the capsule, thus ejecting the medicament which is subsequently inhaled.

UK Patent 2151491 discloses a device having two portions which are telescopically connected, and which define a chamber adapted to receive a capsule loosely in a vertical position. The capsule is pierced by a pair of blades, following which inhalation through the device results in vibration of the capsule and ejection of the medicament which is then inhaled.

The device disclosed in the documents mentioned above have the disadvantage that they must be disassembled and reassembled in order to insert a capsule for each administration of medicament. This is difficult for some patients, particularly the elderly who may have impaired hand movements due to arthritis and the like. In addition, a container of capsules must be carried by the patient throughout the day, and the volume occupied by an inhaler and a container of capsules is too large to be convenient.

SUMMARY OF THE INVENTION

The present invention aims at providing a device for the administration of inhalation medicament held in a capsule which overcomes or substantially mitigates the disadvantages of prior art devices.

According to the present invention, there is provided a device for the administration of inhalation medicament held in a capsule, comprising a chamber adapted to receive a capsule and having an air inlet and an air outlet, capsule piercing means, and a magazine for holding a plurality of capsules, wherein the magazine is rotatably mounted about the air outlet, and there are provided chamber loading means to convey a capsule from the magazine to the chamber.

The device of the present invention has the advantages that a separate container of capsules no longer needs to be carried by a patient, and that the device does not need to be disassembled and reassembled to insert a capsule for each administration of medicament because the chamber loading means conveys the capsule from the magazine to the chamber.

It is preferred that the air outlet be coaxial with the longitudinal axis of the chamber. This makes for a more efficient emptying of the capsule when it is loosely held in a vertical position.

Desirably, the magazine includes an air pathway communicating with the air outlet of the chamber. The air pathway may be through the center of the magazine, and preferably terminates in a mouthpiece portion provided on the magazine. Again, this makes for greater compactness since a separate mouthpiece does not need to be provided.

Preferably, the magazine comprises a plurality of bores each adapted to receive two or more capsules arranged end to end. It is further preferred that the bores be arranged around and coaxially with the air pathway. With this configuration, it is possible to conveniently fit around forty capsules into the magazine. Of course, the number of capsules accomodated by the magazine will depend, amongst other things, upon the size of capsule employed, the number of bores and the length of the magazine.

Preferably, the chamber loading means comprise a slider having a capsule seat adapted to hold a capsule which is moveable between a filling position at which the seat communicates with a bore of the magazine and a loading position at which the seat forms part of the chamber. By this means a capsule may be conveyed from the magazine to the chamber simply by moving the slider, for example, radially. It is further preferred that the slider be movable to a capsule ejecting position intermediate the filling and loading positions and at which emptied capsules may be removed from the device after the administration of the medicament.

Desirably, successive bores of the magazine may be brought into registration with the capsule seat when in the filling position by rotating the magazine. Thus, when all of the capsules from one bore have been used, the capsules held in the next bore may be filled into the capsule seat simply by rotating the magazine.

Desirably, the capsule piercing means can be arranged in a fixed position projecting into the path of movement of the slider.

It is preferred that the capsule piercing means comprise a blade slidably mounted for movement between a rest position at which the blade lies outside the chamber and a piercing position at which the blade extends into the chamber. It is particularly preferred that two such blades be provided as this will enchance the emptying of the capsule.

When the chamber loading means comprise a slider, the blade or blades are preferably mounted in the slider and biased towards the rest position. By situating the blades in the slider, manufacture of the device is simplified since the integral slider and piercing unit may simply be inserted into the rest of the device.

Alternatively, the rotating magazine is provided with ratchet means cooperating with corresponding ratchet means operated by the slider to rotate the magazine simultaneously with the movement of the slider.

BRIEF DESCRIPTION OF THE DRAWINGS

FIG. 1 is a side elevation view of the inhalation device body;

FIG. 2 is a front elevation view of the body of FIG. 1;

FIG. 3 is a cross sectional view taken along line III—III of FIG. 1;

FIG. 4 is a bottom plan view of the body of FIG. 1;

FIG. 5 is a top plan view of the lower closure disc of the inhalation device body of FIG. 1;

FIG. 6 is a sectional view of the rotating magazine of the inhalation device, taken along line VI—VI of FIG. 7;

FIG. 7 is a sectional view of the rotating magazine taken along line VII—VII of FIG. 6;

FIG. 8 is an axial sectional view of the cylindrical cover of the rotating magazine of FIG. 6;

FIG. 9 is a top plan view of the slider operating the rotating magazine of FIG. 6;

FIG. 10 is a sectional view taken along line X—X of FIG. 9;

FIG. 11 is a top plan view of the mouthpiece to be applied on the inhalation device body;

FIG. 12 is an axial sectional view taken through the assembled inhalation device with the slider in an extracted position ready to receive a medicament capsule;

FIG. 13 is a sectional view taken along line XIII—XIII of FIG. 12;

FIG. 14 is a view taken along line XIV—XIV of FIG. 12;

FIG. 15 is a view similar to FIG. 12, but with slider in an inserted position;

FIG. 16 is a sectional view taken along line XVI—XVI of FIG. 15;

FIG. 17 is a view taken along line XVII—XVII of FIG. 15;

DESCRIPTION OF PREFERRED EMBODIMENTS

Figure 18:
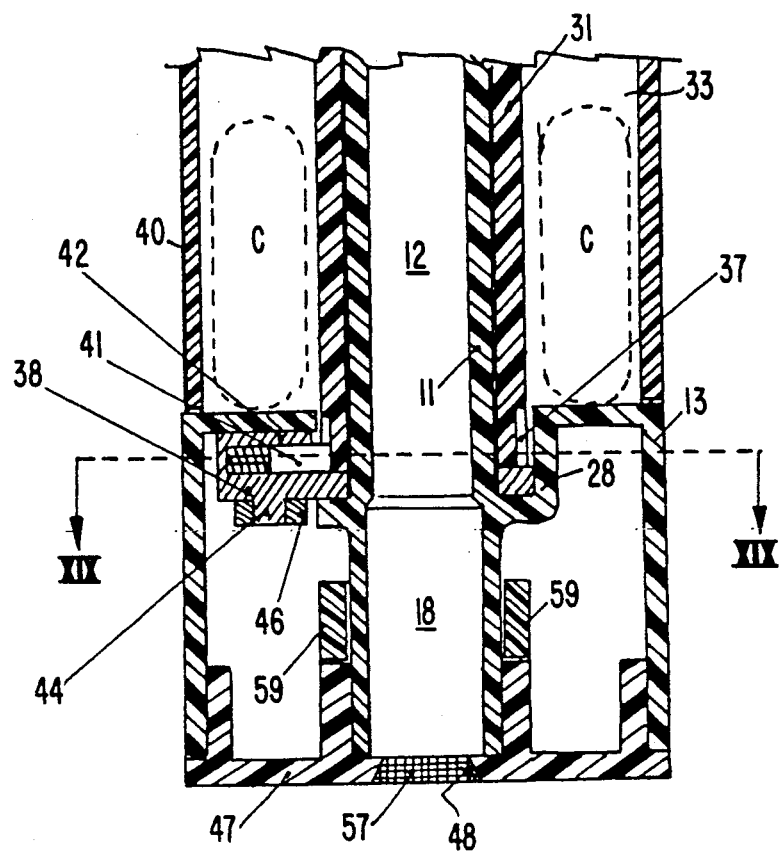
FIG. 18 is a partial axial sectional view taken through another embodiment of the inhalation device according to the invention.

Referring now to FIGS. 1 to 3, there is shown the inhalation device body, generally designated by reference numeral 10. The inhalation device body comprises a tubular portion 11 having an inhalation passage 12. This tubular portion 11 terminates with a base portion 13 substantially cylindrical in shape, connected thereto through a portion 14 having a greater diameter so as to form a step 15. At the upper end of the tubular portion 11 a peripheral groove 27 is formed for receiving a stop ring. The base portion 13 has a pair of concavities 16 defining a front portion 17 which is substantially parallelepipedal in shape. The base portion 13 has a cylindrical chamber 18 which is coaxial with the inhalation passage 12 and communicates with the outside through a slot 19. In its lower portion the chamber 18 communicates with outside through a recess 20. The side walls defining the slot 19 have a pair of confronting concavities 21 forming a pocket for receiving a capsule containing the medicament. Open to the slot 19 are two holes 22, which are formed in the base portion 13 and accomodate the capsule piercing elements P, as will be described later.

As can be seen from FIGS. 4 and 5, recess 20 has a substantially square form and a disc 23 having a substantially square opening 24 is provided, which is to be fastened to the lower surface of the base portion 13, for example by means of screws inserted in the holes 25 of the disc 23 and in the threaded hole 26 of the base portion 13.

In FIGS. 6 and 7 there is illustrated a rotating magazine, generally designated by reference numeral 30. It comprises a tubular body 31 having a central bore 34 and outer longitudinal grooves 33 extending over the whole length of the magazine and defined by equally spaced radial walls 32. Each of these longitudinal grooves 33 accomodates therein a stack of capsules C containing a medicament. The central bore 34 of the rotating magazine 30 has a diameter substantially corresponding to the outer diameter of the tubular portion 11 and receives therein this tubular portion. The bore 34 has at the lower portion thereof an enlargement 35 accomodating the greater diameter lower portion 14 of the tubular portion 11 and forming a step 36 on which the step 35 of the tubular portion 11 rests.

In FIG. 8 there is shown a cylindrical cover 40 having an inner diameter corresponding to the outer diameter of the walled portion of the rotating magazine 30 and this cylindrical cover is snugly fitted on the rotating magazine so as to close the grooves 33 accommodating the medicament capsules. This cylindrical cover is preferably made of a transparent plastic material.

The device is completed by a slider, generally designated by reference numeral 50 and illustrated in FIGS. 9 and 10. This slider has a rectangular base plate 51 having two opposite lugs 52 and an arcuate front plate 53 acting as a gripping element for the slider. On the base plate 51, along the center line of the slider 50, a guide wall 54 is provided and in the base plate 51 a hole 55 is formed which has a lower counterbore 56. This hole receives a filter element 57 forming the bottom of the capsule receiving chamber 18 when the slider 50 is in the inserted position. The guide wall 54 is provided with recesses 58 for receiving the piercing elements P of the capsule C. Preferably, the piercing elements P are in the form of a blade.

A mouthpiece 60 is provided (see FIG. 11) having a hole 61 which is coaxially arranged with respect to the inhalation passage 12 of the tubular portion 11. This hole 61 enlarges at the upper portion thereof with a flaring portion 62 so as to form an elliptical mouthpiece 63 for a patient inhaling the medicament from the device.

The so far described device is assembled in the following manner.

On the tubular portion 11 of the body 10 the rotating magazine 30 is firstly inserted by fitting this tubular portion 11 in the bore 34 of the rotating magazine 30 until the step 36 of this bore 34 is resting against the step 15 of the tubular portion 11. In so doing, the magazine 35 is rotatably supported on the tubular portion 11. Then, in the groove 27 of the tubular portion 11 a stop ring 28 is applied, which holds the magazine 30 in the assembled condition. Thereafter, on the rotating magazine 30 the cylindrical cover 40 is forcedly fitted. In so doing, the longitudinal grooves 33 of the rotating magazine 30 are closed by the cylindrical cover 40, thereby defining the seats for receiving the medicament capsules C. Then, on the assembly including the tubular portion 11, the magazine 30 and the cylindrical cover 40 the mouthpiece 60 is applied, as shown in FIGS. 12 and 15.

Thereafter, in the base portion 13 of the body 10 the slider 60 is inserted so that the base plate 51 thereof enters the recess 20 and the lugs 52 rest against the walls defining the sides thereof, whereas the guide wall 54 extend through the slot 19 of the base portion 13. Then, on the bottom of the base portion 13 the closure disc 23 is applied, which retains the base plate 51 of slider 50 in the recess 20. Thus, the device is assembled and is ready to be used when in the seats defined by the grooves 33 of the rotating magazine 30 and by the cylindrical cover 40 the capsules C containing the medicaments to be inhaled are introduced, as shown in FIGS. 12 and 15.

The operation of the above-mentioned device is as follows.

In the rest position, the slider 50 is inserted in the base portion 13 of the body 10, so that the filter element 57 placed in the hole 55 of the slider base plate 51 is in alignment with the inhalation passage 12 of the tubular portion 11 and with the cylindrical chamber 18 of the base portion 13. When the medicament is to be inhaled, the slider 50 is placed in the position shown in FIG. 12, wherein the capsule receiving pocket 21 of the slot 19 is in alignment with one seat 33, in this case the seat 33a, of the rotating magazine 30 which contains, in this case, four capsules C, so that the lowermost capsule C1 falls down by gravity in the capsule receiving pocket 21 of the slot 19 and stops against the filter element 57. A this point, the slider is introduced in the chamber 18 of the base portion 13, so that the capsule C1 is shifted by the slider guide wall 54 in the chamber 18 which is aligned with the inhalation passage 12 of the tubular portion 11. In so doing, the capsule C1 comes in contact with the piercing elements P so that the capsule is broken at the upper and lower portions thereof and comes in this condition into the chamber 18, as shown in FIG. 15.

In this position, the piercing elements P are in the respective recesses 58 provided in the slider guide wall 54. In the position shown in FIG. 15, the hole 61 of the mouthpiece 60 is aligned with the inhalation passage 12 of the tubular portion 11, the chamber 18 of the base portion 13, the filter element 57 and the opening 24 provided in the lower closure disc 23. Now, the patient can inhale the medicament released by the capsule C1 by applying the mouthpiece 60 against his mouth and by sucking through the inhalation passage 12.

When another inhalation is to be made, the slider 50a is extracted so that the filter element 57 forming the bottom of the device is moved out of register from the chamber 18 and the broken capsule C1 lying in the latter can fall out of the device through the opening 24 of the closure disc 23, while another capsule, for example the capsule C2, can now fall down in the capsule receiving pocket 21 of the slot 19 until it is supported by the filter element 57 and then the insertion operation of the slider 50 is repeated. When the capsules C contained in a seat 33 of the rotating magazine 30 are depleted it is sufficient to rotate the magazine until another seat 33 containing capsules C is in alignment with the capsule receiving pocket 21 of the base portion 13.

In a second embodiment of the device according to the invention the piercing elements P are provided in the slider rather than in the base portion of the body.

Figure 20:
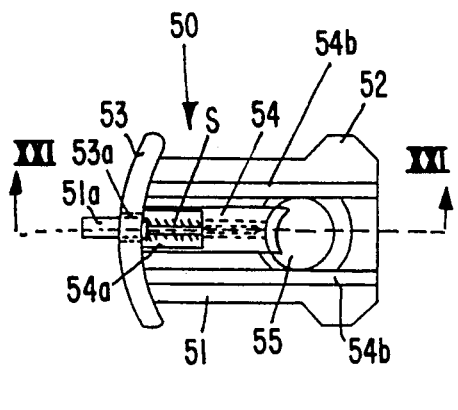
FIG. 20 is a top plan view of another slider of the inhalation device in which the piercing means are provided on the slider.
Figure 21:
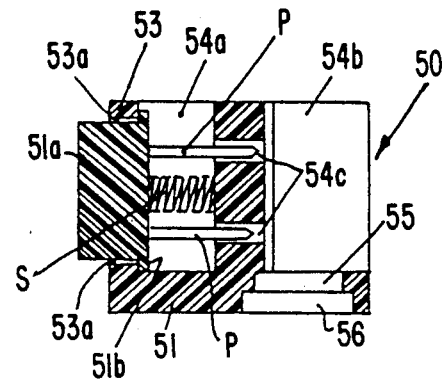
FIG. 21 is a sectional view taken along line XXI—XXI of FIG. 20.

To this purpose, the slider is somewhat modified. This modified slider 50a is shown in FIGS. 20 and 21 and the portions thereof similar to those of the slider 50 are designated by similar references. The guide wall 54 of the slider 50a is provided with a receptacle 54a. Two side walls 54b arranged on either side of the guide wall 54 guide the slider along the base portion 13 of the device. The receptacle 54a communicates with the outside through a slot 53a provided in the arcuate front plate 53 and in this slot 53a a push button 51a is inserted which is provided with the piercing elements P. Push button 51a is retained in the receptacle 54a by a pair of lugs 51b abutting against the arcuate front plate 53 and is biased in the extracted position by a compression spring S arranged between the push button and the inner wall of the receptacle 54a. A pair of holes 54c provided in the guide wall 54 accomodate the piercing elements P.

Figure 22:
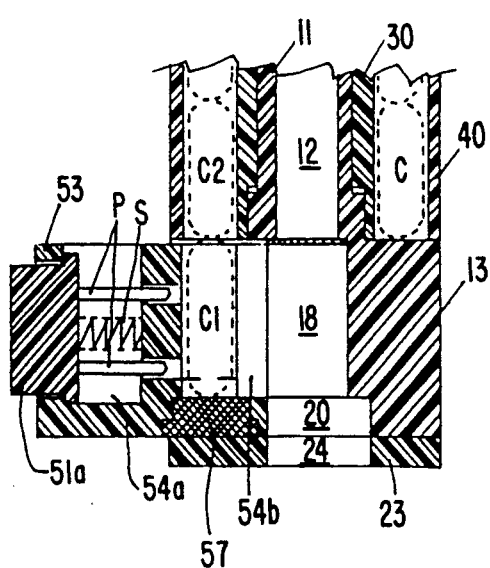
FIG. 22 is a partial sectional view taken through the assembled inhalation device with the slider shown in FIGS. 20, 21 in an extracted position.
Figure 23:
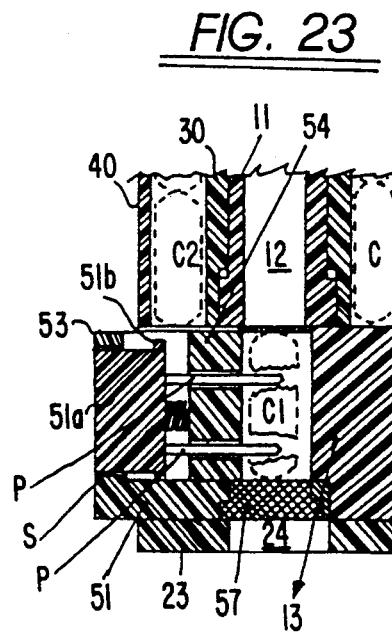
FIG. 23 is a view similar to FIG. 22, but with the slider in an inserted position in which the piercing means are breaking a medicament capsule.

The operation of the device according to this embodiment is the same as in the above-described first embodiment. The only difference is the following. In the rest position the slider 50a is inserted in the base portion 13 of the inhaler body 10. When the medicament is to be inhaled, the slider 50a is placed in the position shown in FIG. 22 which corresponds to the position shown in FIG. 12 of the first embodiment. When the slider 50a is introduced in the chamber 18 of the base portion 13, the capsule C1 is shifted by the slider guide wall 54 in the chamber 18. For breaking the capsule C1 it is necessary to push the push button 51a against the force of the compression spring S so that the piercing elements P are pushed through the holes 54c and in the chamber 18, whereby the capsule C1 therein is broken. This condition is shown in FIG. 23.

Figure 19:
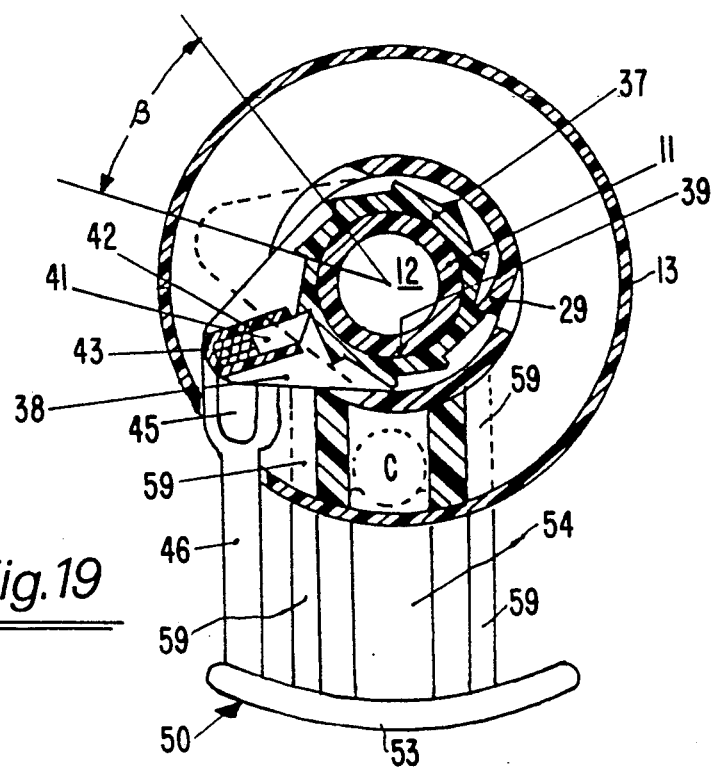
FIG. 19 is a sectional view taken along line XIX—XIX of FIG. 18.

In FIGS. 18 and 19 a third embodiment of the invention is illustrated, which is more sophisticated because instead of manual rotation of the rotating magazine 31 a rotating mechanism is substituted. The elements which are the same as those of the embodiment illustrated in FIGS. 1 to 17 are designated by the same references.

In this embodiment, the base portion 13 has been slightly modified so as to accomodate the rotating mechanism of the magazine 30. As a matter of fact, in the upper wall of the base portion 13 a circular recess 28 is formed for receiving the tubular body 31 of the rotating magazine 30. This tubular body 31 is provided at the lower portion thereof with ratchet teeth 37 (see FIG. 19). Below the ratchet teeth 37 an operating arm 38 is provided, which has a hole 39 and is rotatably arranged in the recess 28. The arm 38 carries at the upper portion thereof a pawl 41 inserted in a cap 42 and biased by a spring 43 towards the outside of the cap. This pawl 41 engages one of the ratchet teeth 37. On the lower surface the arm 38 has a post 44 which engages an eyelet 45 provided at the free end of a rod 46 which is integrally connected to the slider 50 and penetrates the base portion 13 of the inhaler body 10 through a hole 49.

The wall defining the side of the recess 28 is provided with an inwardly biased elastic tongue 29, forming an antirotation stop element for the ratchet teeth 37.

The slider 50, in this case, is slightly modified because, in addition to have the guide wall 54, it has also two guide strips 59 arranged on both sides of the slot 19 of the base portion 13, whereas the closure disc 23 has been substituted by a cover 47 having a center bore 48 in which the filter element 57 is inserted.

The operation of the above described inhaler is as follows:

Starting from the rest position shown in FIG. 15, for making an inhalation it is necessary to extract the slider 50 from the base portion 13 of the inhaler body 10. This extraction movement of the slider 50 causes the rod 46 to rotate the operating arm 38 counterclockwise, while the ratchet teeth 37 (and therefore the rotating magazine 30) remain stationary because the stop tongue 29, being in engagement with a ratchet tooth, prevents a counterclockwise rotation of the rotating magazine. When the slider 50 is arrives at the position shown in FIG. 12, a capsule C1 can fall down in the capsule receiving pocket 21 of the slot 19 until it rests on the base plate 51 of slider 50. Then, the slider 50 is inserted until it is in the position shown in FIG. 15 wherein the capsule C1 has been moved into the chamber 18 of the base portion 13 and, during this movement, has been broken by the piercing elements P. Here again the piercing elements P are preferably in the form of blades. With this insertion movement, the rod 46 of the slider 50 is moved in the base portion 13 until the post 44 of the operating arm 38 strikes against the edge defining the leading end of the eyelet 45. As the insertion movement of the slider 50 continues, the operating arm 38 is rotated in a clockwise direction by an angle $\beta$ which is equal to the pitch of the ratchet teeth and the pawl 41 rotates the ratchet teeth (and therefore the magazine 30) by the same angle $\beta$ so as to bring the next seat 33 of the rotating magazine 30 in alignment with the capsule receiving pocket 21 of the slot 19 of the base portion 13.

In this manner, a capsule contained in the next seat 33 is at disposal for the next inhalation. After each inhalation, the magazine 30 rotates through the angle $\beta$ until all the capsules C contained in the series of seats 33 have been ejected.

Here again the piercing elements P can be arranged in the slider 50a rather than being arranged in the base portion 13 of the inhaler body 10, as shown in FIGS. 20 to 23, and the breaking operation of the capsule C1 is performed by pushing the push button 51a so as to cause the piercing elements P fastened thereto to penetrate the capsule and break it.

As can be seen from the foregoing, the advantages of the inhaler according to the invention include the following:

a) Possibility of making an inhalation by a simple movement of extraction and insertion of the slider without needing the inhaler to be opened for introducing therein a capsule and then to be closed and the capsule piercing means to be acted upon in a separate operation;

b) Possibility of making subsequent inhalations without needing a capsule to be introduced each time in the inhaler;

c) Possibility of rotating the magazine in order to put the capsule seats in alignment with the capsule receiving pocket in the base portion of the inhaler simultaneously with the insertion operation of the slider;

d) Possibility of ejecting the broken capsule after the inhalation operation.

In addition to these great advantages, the inhaler according to the invention lends itself very well to be used as a package for containing the medicament capsules and because of the very low production costs, particularly of the first embodiment, to be put in commerce as such by the same pharmaceutical companies which produce the medicaments to be inhaled and, once all the capsules contained therein have been used, the inhaler can be disposed of.

What is claimed is:

1. A device for administering inhalation medicament in a capsule, said device comprising:

an inhalation device main body including a tubular portion having an inhalation passage extending therein, and a base portion defining a chamber therein adapted to accommodate a capsule and communicating with said inhalation passage and the exterior of the main body;

a magazine supported on said main body, the magazine defining a plurality of bores therein adapted to accommodate a plurality of capsules;

a slider slidably mounted to the base portion of said inhalation device main body and defining a capsule seat therein adapted to accommodate a capsule, said slider being slidable relative to said base portion and to said magazine between a filling position at which said capsule seat is aligned with a respective one of the bores of said magazine and a loading position at which said capsule seat is located in said chamber;

a capsule piercing means for piercing a capsule accommodated in said capsule seat while said slider is located between the filling position and the loading position; and a mouthpiece located at an end of the tubular portion of said inhalation device main body that is remote from the base portion thereof.

2. A device as claimed in claim 1, wherein said bores extend longitudinally of said magazine along respective axes thereof that are parallel to a longitudinal axis of said tubular portion.

3. A device as claimed in claim 1, wherein said capsule piercing means is disposed on said slider.

4. A device as claimed in claim 3, wherein said capsule piercing means includes a blade, and push button means for slidably mounting said blade between a rest position at which said blade lies outside of said chamber while said slider is located in the loading position and a piercing position at which said blade extends into said chamber while said slider is located in the loading position.

5. A device as claimed in claim 1, wherein said capsule piercing means is disposed on the base portion of said inhalation device main body.

6. A device as claimed in claim 5, wherein said capsule piercing means comprises piercing elements extending into a path of movement of said slider.

7. A device as claimed in claim 1, wherein said magazine is rotatably supported on said main body by said tubular portion, and the bores defined by said magazine are located radially of said tubular portion, rotation of said magazine about said tubular portion sequentially aligning said bores with the capsule seat of said slider while the slider is in the filling position thereof.

8. A device as claimed in claim 7, wherein each of said bores are adapted to receive two or more capsules arranged end-to-end.

9. A device as claimed in claim 8, wherein said bores extend longitudinally of said magazine along respective axes thereof that are parallel to a longitudinal axis of said tubular portion.

10. A device as claimed in claim 1, wherein each of said bores are adapted to receive two or more capsules arranged end-to-end.

11. A device as claimed in claim 10, wherein said bores extend longitudinally of said magazine along respective axes thereof that are parallel to a longitudinal axis of said tubular portion.

* * * * *